United States Patent
Campbell (10) Patent No.: US 6,910,770 B2
(45) Date of Patent: Jun. 28, 2005

(54) EYE REFRACTOR WITH ACTIVE MIRROR WAVEFRONT SENSOR

(75) Inventor: Charles E. Campbell, Berkeley, CA (US)

(73) Assignee: Visx, Incorporated, Santa Clara, CA (US)

( * ) Notice: Subject to any disclaimer, the term of this patent is extended or adjusted under 35 U.S.C. 154(b) by 0 days.

(21) Appl. No.: 10/364,766

(22) Filed: Feb. 10, 2003

(65) Prior Publication Data

US 2004/0156015 A1 Aug. 12, 2004

(51) Int. Cl.$^7$ ............................................. A61B 3/10
(52) U.S. Cl. ................................................. 351/205
(58) Field of Search ........................... 351/205, 206, 351/211, 212, 214, 216, 220, 221; 606/4, 5; 356/121, 124, 511, 512, 513

(56) References Cited

U.S. PATENT DOCUMENTS

| | | |
|---|---|---|
| 4,665,913 A | 5/1987 | L'Esperance, Jr. |
| 5,646,791 A | 7/1997 | Glockler |
| 5,683,379 A | 11/1997 | Hohla |
| 5,713,892 A | 2/1998 | Shimmick |
| 5,912,731 A | 6/1999 | DeLong et al. |
| 6,095,651 A | 8/2000 | Williams et al. |
| 6,203,539 B1 | 3/2001 | Shimmick et al. |
| 6,271,915 B1 | 8/2001 | Frey et al. |
| 6,278,100 B1 | 8/2001 | Friedman et al. |
| 6,338,559 B1 | 1/2002 | Williams et al. |
| 6,347,549 B1 | 2/2002 | Ryan et al. |
| 6,428,533 B1 | 8/2002 | Bille |
| 6,595,643 B2 * | 7/2003 | Levine .................. 351/221 |
| 6,673,062 B2 | 1/2004 | Yee et al. |
| 6,685,319 B2 | 2/2004 | Watson et al. |
| 2002/0047992 A1 | 4/2002 | Graves |

OTHER PUBLICATIONS

U.S. patent application Ser. No. 2002–135736, Stark et al., filed Sep. 26, 2002.
U.S. patent application Ser. No. 2003–0223037, Chernyak, filed Dec. 04, 2003.

* cited by examiner

Primary Examiner—George Manuel
(74) Attorney, Agent, or Firm—Townsend and Townsend and Crew LLP (57) ABSTRACT

Methods and systems for measuring optical aberrations of an eye are provided. In one embodiment, the present invention provides transmitting light from the eye along an optical path to an aberration sensor. An adaptive optic is disposed along the optical path between a target optical system and the aberration sensor. Aberrations of the adaptive optic can be adjusted in response to a signal generated by the aberration sensor so as to provide a desired sensed aberration. The shape of the adjusted adaptive optic can be determined with the aberration sensor by transmitting an adaptive optic configuration measurement beam along the optical path.

48 Claims, 7 Drawing Sheets

EYE REFRACTOR WITH ACTIVE MIRROR WAVEFRONT SENSOR

CROSS-REFERENCES TO RELATED APPLICATIONS

The present application is related to U.S. patent application Ser. No. 10/006,992, filed on Dec. 6, 2001, Ser. No. 09/960,163, filed on Sep. 20, 2001; and 60/356,657, filed on Feb. 11, 2002, the complete disclosures of which are incorporated herein by reference.

BACKGROUND OF THE INVENTION

The present invention relates generally to laser eye surgery methods and systems. More specifically, the present invention relates to methods and systems for measuring complex optical aberrations of the human eye.

Laser eye surgical systems typically employ a system that can track and measure the optical characteristics and errors of a patient's eye. One promising eye measurement system uses wavefront technology that allows the surgeon to measure and treat low order and high order aberrations in and on the patient's eye. A wavefront measurement of the eye creates a high order aberration map that permits assessment of aberrations throughout the optical pathway of the eye, e.g., both internal aberrations and aberrations on the corneal surface. The aberration information can then be used to compute a custom ablation pattern so that the surgical laser system can correct the complex aberrations in and on the patient's eye.

One exemplary wavefront technology system uses Hartmann-Shack wavefront sensors that can quantify aberrations throughout the entire optical system of the patient's eye, including first and second-order sphero-cylindrical errors, coma, and third and fourth-order aberrations related to coma, astigmatism, and spherical aberrations.

For example, as is described in U.S. Pat. No. 6,095,651, one method of analyzing the high-order aberrations in the patient's eye is through the use of a deformable mirror. The wavefront aberrations can be measured by a wavefront sensor and the deformable mirror can be deformed via control signals from the wavefront sensors to compensate for the wavefront aberration of the eye, until the error in the measured wavefront aberration reaches an asymptotic value. At that point the deformable mirror has taken an appropriate shape to provide wavefront compensation for the aberrations of the eye. Unfortunately, the adjusted shape of the deformable mirror does not directly indicate to the physician the actual aberrations of the patient's eye. Consequently, it is often required to apply a complicated calibration scheme so that the control signals used to deform the deformable mirror may be correlated with the aberrations from the patient's eye that the deformed mirror removes.

Consequently, what are needed are devices and methods which can determine the aberrations of the patient's eye, without having to employ a complicated calibration method.

BRIEF SUMMARY OF THE INVENTION

The present invention provides systems and methods for measuring a wavefront measurement of a patient's eye and for determining optical aberrations in the patient's eye.

In one aspect, the present invention provides a method for measuring an optical aberration of a target optical system. The method comprises transmitting light from the target optical system along an optical path to an aberration sensor. An adaptive optic can be disposed along the optical path between the target optical system and the sensor. The adaptive optic is adjusted in response to a signal generated by the aberration sensor so as to provide a desired sensed aberration. The shape of the adjusted adaptive optic is determined by transmitting an adaptive optic configuration measurement beam along the optical path.

In another method of the present invention, a light is transmitted from the eye along an optical path to an aberration sensor. An adaptive optic is disposed along the optical path between a target optical system and the aberration sensor. The adaptive optic is adjusted in response to a signal generated by the aberration sensor so as to provide a desired sensed aberration (e.g., no aberrations). The shape of the adjusted adaptive optic is determined by transmitting an adaptive optic configuration measurement beam along the optical path. In a particular configuration, the measurement beam is a collimated beam that has a perfect wavefront prior to being transmitted onto the adaptive optic and any aberrations introduced into the collimated beam will indicate the shape of the adaptive optic.

In another aspect, the present invention provides a system for measuring optical aberrations of an eye. In one embodiment, the system comprises an aberration sensor disposed along an optical path oriented for receiving light from an eye. An adaptive optic can be disposed along the optical path between the eye and the sensor. A feedback controller can adjust the adaptive optic in response to a signal generated by the sensor so as to provide a desired sensed aberration. A configuration beam source is optically coupled to the optical path between the eye and the adaptive optic. A processor receives configuration signals from the aberration sensor when the configuration beam is transmitted onto the adaptive optic and aberration sensor. The configuration signals are generated in response to the configuration beam and the processor can determine a configuration of the adaptive optic based on the configuration signals.

In another embodiment, the present invention provides a system for measuring optical aberrations of an eye. The system includes means for transmitting light from the eye along an optical path to an aberration sensor means. An adaptive optic means can be disposed along the optical path between the eye and the aberration sensor means. Means for adjusting aberrations of the adaptive optic means in response to a signal generated by the aberration sensor means can be provided so as to provide a desired sensed aberration. The system can further include means for determining the shape of the adjusted adaptive optic means for measuring the optical aberrations of the eye.

In another embodiment, the present invention provides a system for measuring optical aberrations of an eye. The system comprises an aberration sensor positioned along an optical path that is oriented for receiving light transmitted from the eye. An adaptive optic is disposed along the optical path between the eye and the aberration sensor. A feedback controller adjusts the adaptive optic in response to a feedback signal generated by the aberration sensor so as to provide a desired sensed aberration. An adaptive optic measurement beam source is positioned to deliver a measurement beam on the optical path to the adjusted adaptive optic. The feedback controller receives a configuration signal from the aberration sensor that is generated in response to aberrations imparted into the measurement beam by the adjusted adaptive optic. The feedback controller determines optical aberrations of the eye by determining the configuration of the adjusted adaptive optic based on the aberrations in the measurement beam that are sensed by the aberration sensor.

For a further understanding of the nature and advantages of the invention, reference should be made to the following description taken in conjunction with the accompanying drawings.

DETAILED DESCRIPTION OF THE INVENTION

Figure 1:
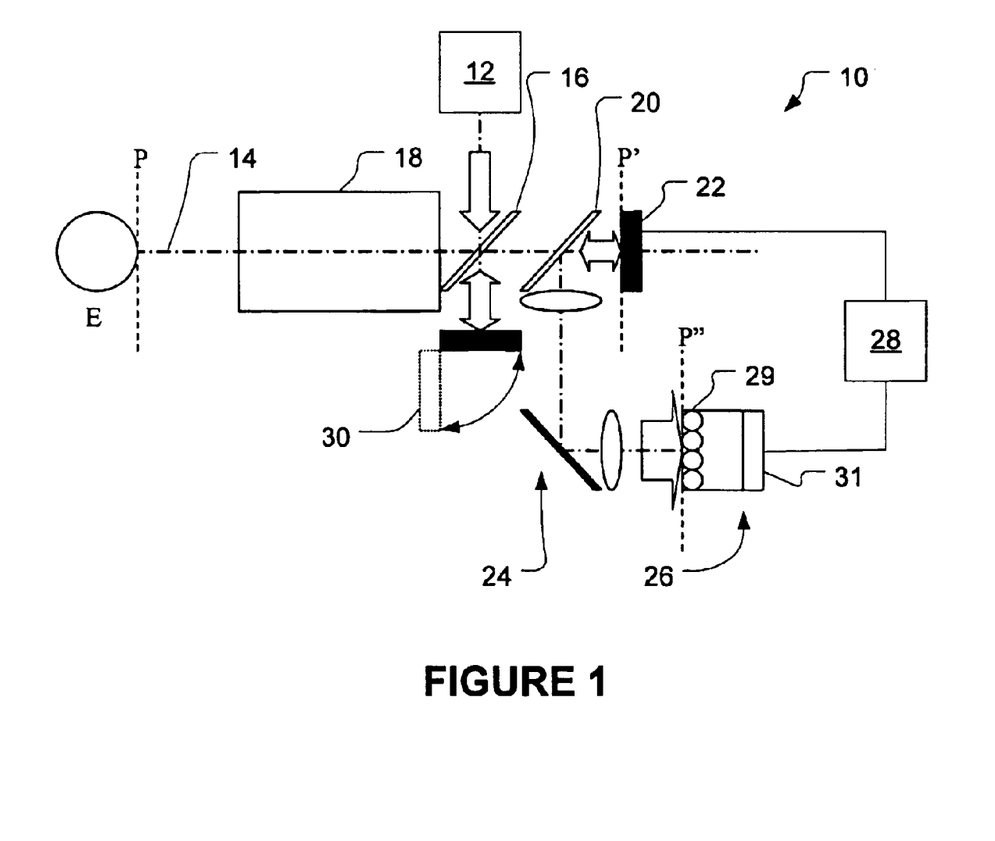
FIG. 1 schematically illustrates a simplified wavefront measurement system that encompasses the present invention.
Figure 2:
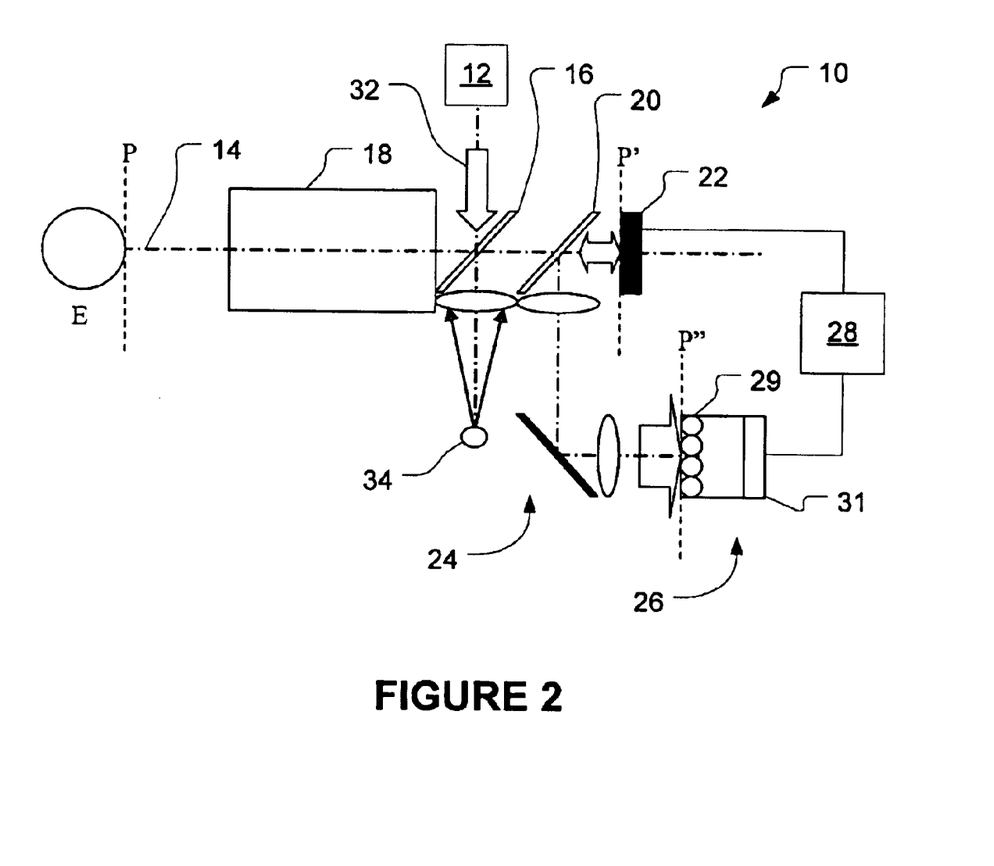
FIG. 2 illustrates another simplified wavefront measurement system that encompasses the present invention.

FIGS. 1 and 2 illustrate simplified embodiments of wavefront measurement systems 10 that encompass the present invention. As can be appreciated, the illustrated wavefront measurement systems 10 are merely examples of some wavefront measurement systems that can be used with the present invention and other conventional or proprietary wavefront measurement systems with other configurations of optical elements, wavefront sensors, and the like, can be used without departing from the scope and spirit of the present invention.

As shown in FIG. 1, wavefront measurement system 10 typically includes a light source 12, such as an infrared LED, super luminescent LED, a laser, or the like. In one embodiment, the illumination light will have a diameter that is large enough to flood the pupil of the eye with light. In other embodiments, however, the illumination light may have a diameter that does not fill the pupil of the eye, which will be described in more detail below. Light source 12 can be used to project an illumination light through optical tissues of the eye so as to form an image upon a surface of the retina of the patient's eye E. Optionally, a shutter (not shown) can be positioned in an optical path 14 of the illumination light to control the transmission of the illumination light into and out of the patient's eye E.

A first beam splitter 16 can be positioned in the optical path of the illumination light so as to separate the illumination light into two beams of light. In one configuration, first beam splitter 16 is a 50% beam splitter so that 50% of the illumination light is transmitted toward the eye E and 50% of the illumination light is allowed to pass through the beam splitter and exit the system. As can be appreciated, other types of conventional or proprietary beam splitters can be used in the system 10 without departing from the scope or spirit of the present invention.

The illumination light from light source 12 can be transmitted through compensation optics 18 that are positioned in the optical path 14 of the illumination light. Compensation optics 18 can remove lower order aberrations (e.g., defocus and astigmatism), or the like. The illumination light will enter the pupil of the eye E be transmitted through the optical tissues of the eye and reflect off the retina of the eye. The light reflected from the retina picks up the aberrations in the optical tissues of the eye and the exiting wavefront forms a distorted wavefront at the pupil (e.g., a pupil conjugate plane P) that corresponds to the internal and external errors of the optical tissues in the eye.

The distorted wavefront can then be directed back through compensation optics 18 and onto the first beam splitter 16, where in the illustrated embodiment, 50% of the reflected light is transmitted to a second beam splitter 20 and 50% of the light passes through the beam splitter and is not returned back into the system. At second beam splitter 20, 50% of the distorted wavefront is directed onto an adaptive optic, such as an active or deformable mirror 22, where a pupil conjugate plane P' is formed. The other 50% of the light from the eye will not be returned to the system.

From adaptive optic 22, the distorted wavefront can be transmitted through an optical relay system 24 that can include one or more optical elements such as lenses, mirrors, and/or beam splitters (e.g., polarizing, non-polarizing, etc.). From optical relay system 24, the distorted wavefront will be directed onto an aberration sensor or wavefront sensor 26, such as a Hartmann-Shack sensor. As can be appreciated to those of ordinary skill in the art, a variety of other types of sensors can be used to measure the wavefront that is transmitted from the eye. For example, a moire deflectormeter system, a segmented phase plate/shearing interferometry system, a direct curvature measurement method, or the like can be used instead of or in addition to the Hartmann-Shack sensor.

The distorted wavefront can form a pupil conjugate plane P" in the plane of a lenslet array 29 of the Hartmann-Shack sensor 26. As the image from the retina is transmitted through optical tissues of the eye and imaged onto a surface of lenslet array 29, the lenslet array separates the transmitted image into an array of beamlets, and (in combination with other optical components of the system) images the separated beamlets on the surface of sensor 31. Sensor 31 typically comprises a charged couple device or CCD, and senses the characteristics of these individual beamlets, which can be used to determine the characteristics of an associated region of optical tissues. In particular, where the image comprises a point or small spot of light, a location of the transmitted spot as imaged by a beamlet can directly indicate a local gradient of the associated region of optical tissue.

Once the distorted wavefront from the patient's eye is measured by the wavefront sensor 26, the wavefront sensor can output a feedback signal to a computer controller 28 to indicate the optical errors in the impinging wavefront. Computer controller 28 can transmit a correction signal, that corresponds to the feedback signal, so as to activate the adaptive optic. In one embodiment, the correction signal will act to deform adaptive optic 22 to compensate for the distorted wavefront that is transmitted from the eye. The correction signals can be continued until the wavefront that is transmitted to the wavefront sensor provides a desired sensed aberration. In one embodiment, the adaptive optic will be deformed until the wavefront that is transmitted to the wavefront sensor is substantially nulled (e.g., no aberrations in the wavefront).

Once the wavefront is nulled, the illumination light beam can be stopped or prevented from reaching the eye (e.g., the shutter is moved into position in the optical path) and an optical element 30, such as a back reflection mirror, can be manually or automatically moved into optical path 14 so that the illumination light beam is transmitted onto the adaptive optic 22 without reflecting of the patient's eye. In such embodiments, no extra source of light is required.

In the embodiment illustrated in FIG. 1, optical element 30 can be removably positioned in the optical path of the system such that during the eye measurement, light that passes through first beam splitter 16 is not returned to the optical system. However, after the eye measurement process is completed, the optical element 30 can be positioned in the optical path of the illumination light so that the light that passes through beam splitter 16 can be directed back into the optical system. In one embodiment, the illumination light is a collimated beam of light that has substantially the same wavelength as the illumination beam of light. In other embodiments, however, the illumination light may be uncollimated, and compensation optics (not shown) can be positioned between optical element 30 and adaptive optic 22 to collimate the illumination light.

The collimated light introduced onto the adaptive optic will have a "perfect" wavefront. As the perfect wavefront is transmitted off of the adaptive optic 22, the wavefront will pick up the errors from the shape of the adjusted adaptive optic 22. The wavefront that reaches the wavefront sensor will represent the correction that is imparted by the adaptive optic and an "opposite" of the wavefront error that is imparted by the adaptive optic will be the error of the eye.

Another embodiment of a system 10 that encompasses the present invention is illustrated in FIG. 2. The embodiment illustrated in FIG. 2 is generally used when the illumination light beam 32 generated by light source 12 is not wide enough to fully fill the active mirror and/or has a smaller diameter than the pupil of the eye. By using a small diameter source beam, the aberrations of the eye do not appreciably affect the formation of a small well formed spot on the retinal surface because the aberrations of the eye are essentially filtered by a pinhole optic affect.

In such embodiments, a second light source 34 is needed. Similar to above, in some embodiments, second light source 34 can provide a collimated beam of light. In other embodiments, second light source 34 can provide an un-collimated beam of light, and compensation optics (not shown) can be introduced into the optical path of the second light beam 36 to collimate the light from the second light source.

The embodiment in FIG. 2 generally contains the same elements as the embodiment illustrated in FIG. 1. The primary difference of the embodiment of FIG. 2 is the use of a separate light source 12 for the eye measurement procedure and a separate light source 34 for the adaptive optic measurement beam. As described above in relation to FIG. 1, light source 12 can be used to perform the wavefront measurement of the eye using an illumination light beam 32. Once the wavefront measurement of the eye is completed, light source 12 is turned off or light is otherwise prevented from being reflected off of the patient's eye, and light source 34 is turned on so as to direct a perfect wavefront onto adaptive optic 22. In the illustrated embodiment, light source 34 can transmit a light off of beam splitter 16 and onto adaptive optic 22. As the perfect wavefront is reflected off of adaptive optic 22, the wavefront will pick up the errors from the shape of the adjusted adaptive optic 22. The wavefront that reaches the wavefront sensor will represent the correction that is imparted by the adaptive optic and an "opposite" of the wavefront error that is imparted by the adaptive optic will be the error of the eye.

While not shown, systems 10 of the present invention can further include an imaging assembly, such as a CCD device that can capture an image of the patient's eye during the wavefront measurement. A more complete description of an exemplary wavefront system can be found in U.S. Pat. No. 6,095,651 and co-pending U.S. patent application Ser. No. 10/300,714, filed Nov. 19, 2002, the complete disclosure of which is incorporated herein by reference.

The components of one embodiment of a wavefront system for measuring the eye and ablations comprise elements of a VISX WaveScan™, available from VISX, Inc. of Santa Clara, Calif. A preferred embodiment includes a WaveScan with a deformable adaptive optic 22 as described above. An alternate embodiment of a wavefront measuring device is described in U.S. Pat. No. 6,271,915, the full disclosure of which is incorporated herein by reference. It should be appreciated, however, that the wavefront measurement systems of FIGS. 1 and 2 are merely examples of configurations that can be used to determine the errors of a patient's eye, and a variety of other configurations of beam splitters, compensation optics, lights sources, adaptive optics 22, and wavefront sensors 26 can be used without departing from the present invention.

Figure 3A:
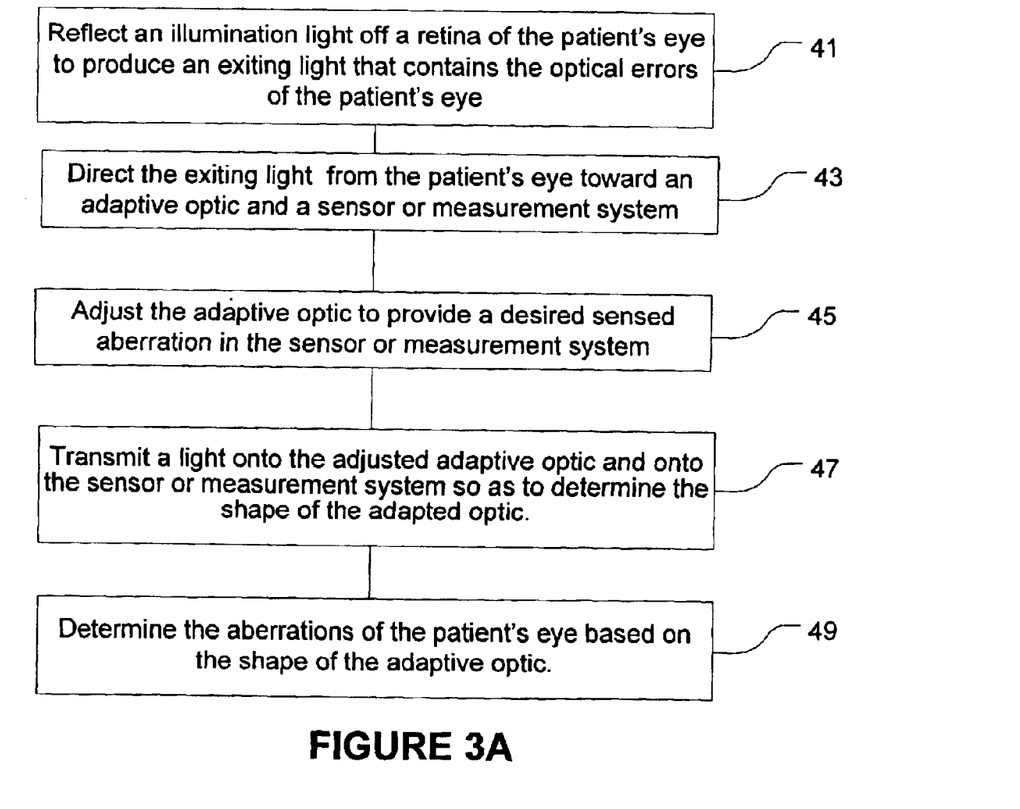
FIG. 3A schematically illustrates a simplified method of measuring an optical aberration of an eye.

FIG. 3A schematically illustrates a simplified method of the present invention. The method comprises reflecting an illumination light off of a retina of the patient's eye so that an exiting light from the eye contains the optical errors of the optical tissues of the eye, Step 41. The exiting light can be directed toward an adaptive optic and reflected off of the adaptive optic onto a sensor or measuring system, Step 43. The adaptive optic can be adjusted (e.g., deformed) until the light reflected from the adjusted adaptive optic provides a desired sensed aberration, Step 45. In one embodiment, the desired sensed aberration is a nulled wavefront. In other embodiments, however, the desired sensed aberration can take other forms. At Step 47, a light is transmitted onto the adjusted adaptive optic and directed to the sensor or measurement system so that the shape of the adapted optic can be determined. From the shape of the adjusted adaptive optic, the aberrations in the patient's eye can be measured, Step 49. In one embodiment, the light in Step 47 is a collimated light that does not have aberrations. In other embodiments, the light may be a steered light, as will be described in greater detail below.

Figure 3B:
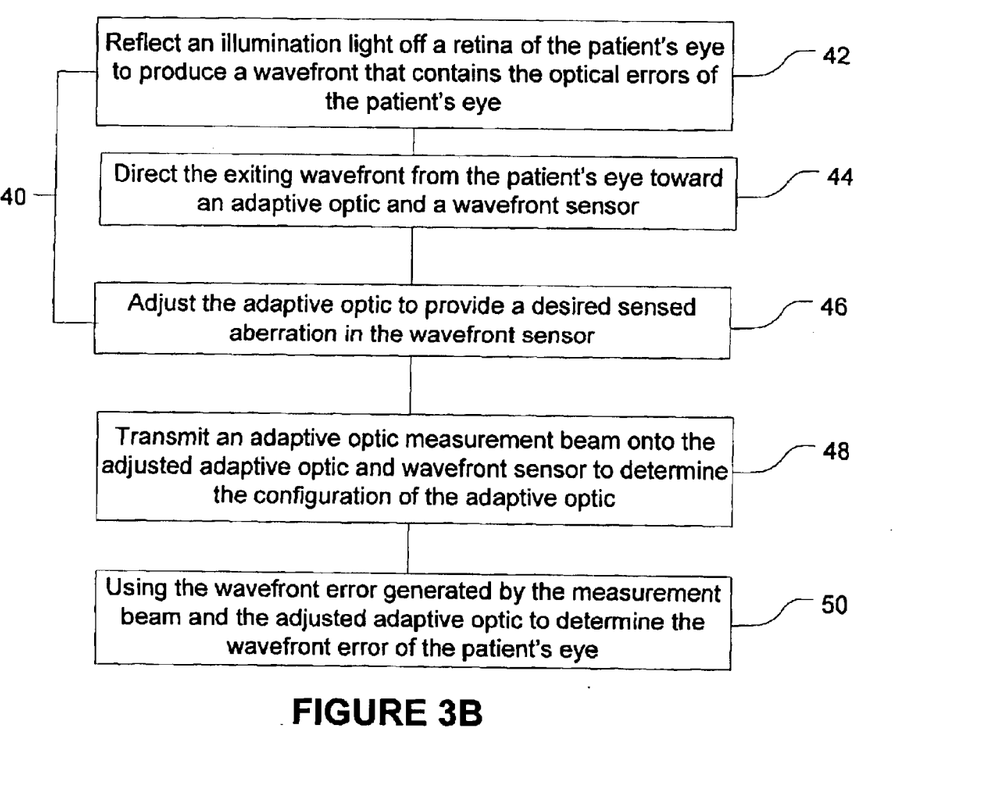
FIG. 3B schematically illustrates one particular embodiment of a method of measuring an optical aberration of an eye.

FIG. 3B schematically illustrates one specific embodiment of a method of the present invention. The method comprises measuring the optical errors of a patient's eye, Step 40. One method of measuring the optical errors of a patient's eye 40 is illustrated as Steps 42 to 46. At Step 42, an illumination light can be reflected off of a retina of the patient's eye to generate an exiting wavefront that contains the optical errors of the optical tissues of the eye. The wavefront can be directed toward an adaptive optic and reflected off of the adaptive optic onto a wavefront sensor, Step 44. A feedback signal from the wavefront sensor can be used to adjust the adaptive optic (e.g., deform a deformable mirror) until the wavefront reflected from the adjusted adaptive optic provides a desired sensed aberration, Step 46. In one embodiment, the desired sensed aberration is a nulled wavefront.

An adaptive optic measurement beam can be transmitted to the adaptive optic and aberration sensor to determine the configuration of the adjusted adaptive optic Step 48. In one embodiment, the measurement beam is a collimated beam that has a perfect wavefront. When the perfect wavefront reflects off of the adjusted adaptive optic, it will pick up the optical aberrations of the adjusted adaptive optic and carry the optical aberrations onto the aberration sensor. The shape of the adjusted adaptive optic can then be determined to determine the optical aberrations (wavefront measurement) of the patient's eye, Step 50. In the illustrated embodiment, the optical aberrations of the patient's eye will be opposite of the wavefront error of the adjusted adaptive optic.

Figure 4:
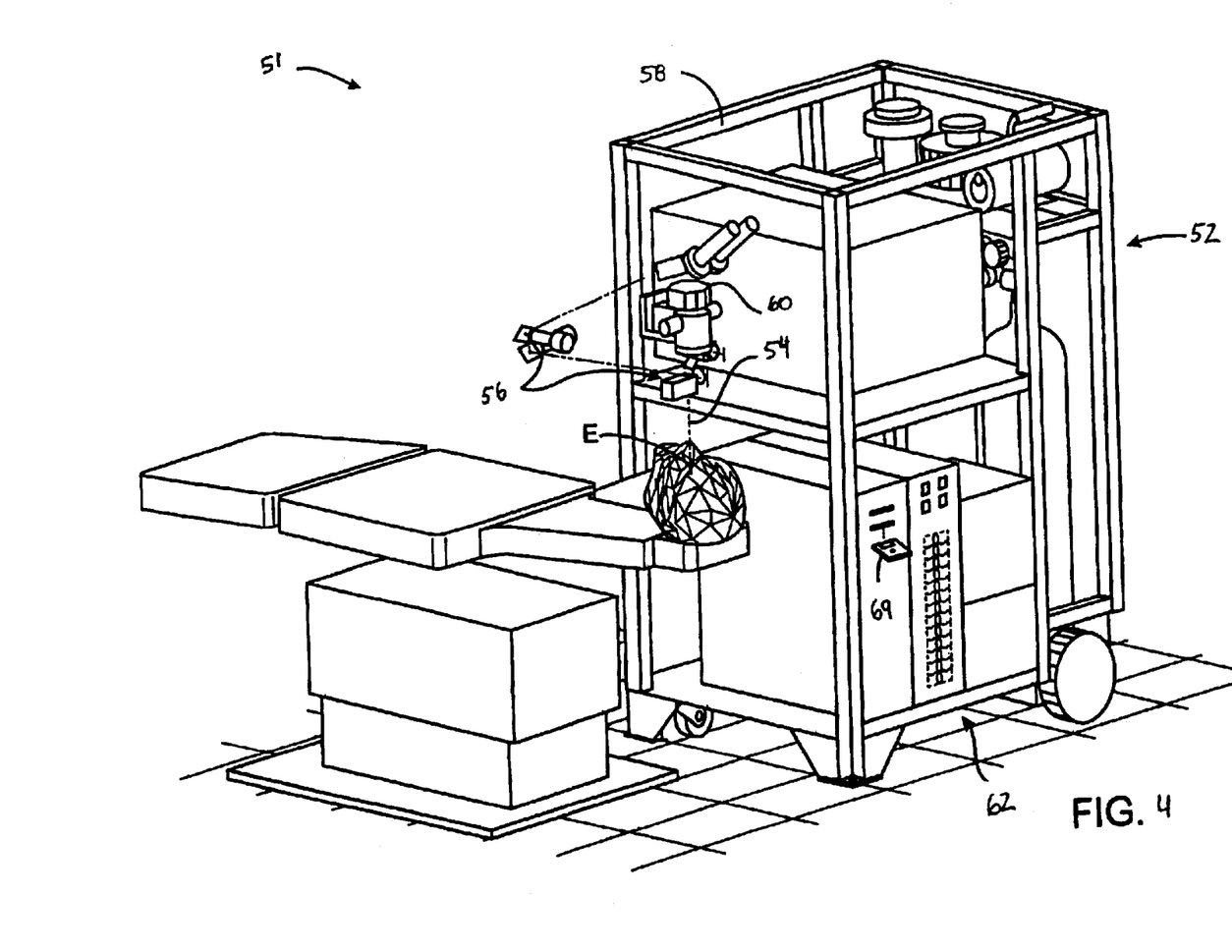
FIG. 4 illustrates a laser surgery system that can be used with the wavefront measurement systems of the present invention.

FIG. 4 illustrates one embodiment of a laser system 51 that can be used with the wavefront measurement system 10 of the present invention. Laser eye surgery system 51 includes a laser 52 that produces a laser beam 54. Laser 52 is optically coupled to laser delivery optics 56, which directs laser beam 54 to an eye of patient P. A delivery optics support structure (not shown here for clarity) extends from a frame 58 supporting laser 52. A microscope 60 is mounted on the delivery optics support structure, the microscope often being used to image a cornea of eye E.

Laser 52 generally comprises an excimer laser, typically comprising an argon-fluorine laser producing pulses of laser light having a wavelength of approximately 193 nm. Laser 52 will preferably be designed to provide a feedback stabilized fluence at the patient's eye, delivered via delivery optics 56. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 205 nm and/or those which utilize frequency-multiplying techniques. Hence, although an excimer laser is the illustrative source of an ablating beam, other lasers may be used in the present invention.

Laser 52 and delivery optics 56 will generally direct laser beam 54 to the eye of patient P under the direction of a computer processor 62. Processor 62 will generally selectively adjust laser beam 54 to expose portions of the cornea to the pulses of laser energy so as to effect a customized ablation profile or treatment program map that is based on the wavefront measurement of the eye so as to sculpt the cornea and alter the refractive characteristics of the eye.

In some embodiments, the treatment program map may be calculated from the wavefront measurements of the eye so as to remove the regular (spherical and/or cylindrical) and irregular errors of the optical tissues. The treatment program map will often be based on both the measured optical properties of the eye and on the characteristics of the corneal tissue targeted for ablation (such as the ablation rate, the refractive index, the propensity of the tissue to form "central islands" or decreased central ablation depths within a uniform energy beam, and the like). The results of the calculation will often comprise an ablation pattern in the form of an ablation table listing ablation locations, numbers of pulses, ablation sizes, and or ablation shapes to effect the desired refractive correction. An exemplary method and system for preparing such an ablation table is described in co-pending U.S. patent application Ser. No. 09/805,737 filed on Mar. 13, 2001 and entitled "Generating Scanning Spot Locations for Laser Eye Surgery," the full disclosure of which is incorporated herein by reference. Ablation table may optionally be optimized by sorting of the individual pulses so as to avoid localized heating, minimize irregular ablations if the treatment program is interrupted, and the like.

In many embodiments, both laser 54 and the laser delivery optical system 56 will be under computer control of processor 62 to effect the desired laser sculpting process, with the processor ideally altering the ablation profile in response to inputs from the optical feedback system. The feedback will preferably be input into processor 62 from an automated image analysis system, or may be manually input into the processor by a system operator using an input device in response to a visual inspection of analysis images provided by the optical feedback system. Processor 62 will often continue and/or terminate a sculpting treatment in response to the feedback, and may optionally also modify the planned sculpting based at least in part on the feedback.

Processor 62 may comprise (or interface with) a conventional PC system including the standard user interface devices such as a keyboard, a display monitor, and the like. Processor 62 will typically include an input device such as a magnetic or optical disk drive, a CD drive, an internet connection, or the like. Such input devices will often be used to download a computer executable code from a computer network or a tangible storage media 69 embodying steps or programming instructions for any of the methods of the present invention. Tangible storage media 69 includes, but is not limited to a CD-R, a CD-RW, DVD, a floppy disk, an optical disk, a data tape, a non-volatile memory, or the like, and the processor 62 will include the memory boards and other standard components of modem computer systems for storing and executing this code.

Laser beam 54 may be adjusted to produce the desired sculpting using a variety of alternative mechanisms. The laser beam 54 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. No. 5,683,379, and as also described in co-pending U.S. patent application Ser. No. 08/968,380, filed Nov. 12, 1997; and Ser. No. 09/274,999 filed Mar. 22, 1999, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913 (the full disclosure of which is incorporated herein by reference) and as demonstrated by other scanning laser systems such as the LSX laser by LaserSight, LadarVision by Alcon/Autonomous, and the 217C by Technolas; using masks in the optical path of laser beam 54 which ablate to vary the profile of the beam incident on the cornea, as described in U.S. patent application Ser. No. 08/468,898, filed Jun. 6, 1995 (the full disclosure of which is incorporated herein by reference); hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 51, as should be understood by those of skill in the art. For example, spatial and/or temporal integrators may be included to control the distribution of energy within the laser beam, as described in U.S. Pat. No. 5,646,791, the disclosure of which is incorporated herein by reference. An ablation effluent evacuator/filter, and other ancillary components of the laser surgery system which are not necessary to an understanding of the invention, need not be described in detail for an understanding of the present invention.

Figure 5:
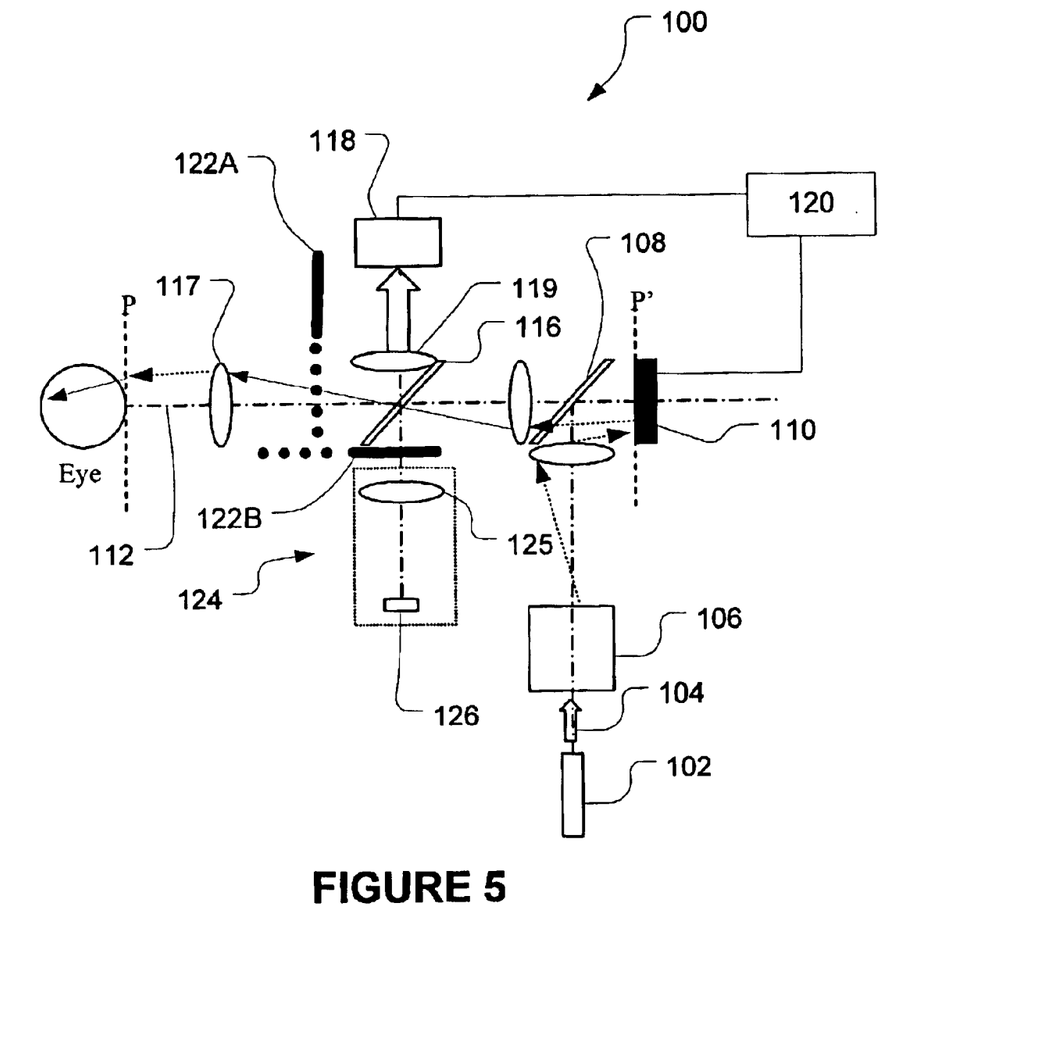
FIG. 5 illustrates an alternative wavefront measurement system that encompasses the present invention.

While all the above is a complete description of the preferred embodiments of the inventions, various alternatives, modifications, and equivalents may be used. For example, as shown in FIG. 5, instead of generating a perfect wavefront illumination light, the present invention may also be used with a system which uses a spatially resolved refractor that deflects rays entering the patient's eye until the rays hit a predetermined spot on the retina. The amount of deflection of the rays required to hit the predetermined spot will substantially corresponds to the wavefront error. Some exemplary systems that can use the present invention are ray tracing or a Tscherning aberrometer system.

FIG. 5 illustrates an exemplary system that provides a "perfect eye" to determine the wavefront errors of the patient's eye. FIG. 5 illustrates a system 100 that includes a beam source 102 that produces a beam 104 for eye measurement. Source beam 104 may be transmitted through beam steering optics 106, such as a galvanometer mirror assembly, acousto-optic beam deflection systems, or the like so as to steer the beam 104 onto a predetermined spot on the eye. Source beam 104 may be a collimated light and may have a diameter between approximately 0.5 mm and 1.5 mm, and typically about 1 mm. Beam steering optics 106 may steer the source beam 104 onto a beam splitter 108, where a portion of the source beam is directed onto an adaptive optic 110. Adaptive optic 110 may take the form of a deformable mirror, but may take the form of any other element that can be actively steer the source beam 104.

Source beam 104 may then be directed from adaptive optic 110 along an optical axis 112 of the patient's eye through a variety of optical elements (e.g., one or more additional beam splitters 116, lenses 117, etc.) and onto the patient's eye. The light rays entering the eye are reflected off of the retina and back out through the optical tissues of the patient's eye. The light beams that exit the patient's eye may be transmitted off of beam splitter 116, where a portion of the light rays emitted from the patient's eye may be directed through one or more optical elements 119 and to a measuring system 118. Measuring system 118 may take many forms, but one useful embodiment comprises a CCD assembly that can obtain images of the light beam spots on the patient's retina. Other forms of measuring system 118 include discrete diode array sensors, and the like.

A shape of adaptive optic 110 may be automatically altered by a control system 120 or manually altered by a user until all of the rays of the source beam entering the patient's eye hit a substantially same point on the retina and no aberrations are measured in the light directed from the eye onto measuring system 118.

During adjustment of the adaptive optic, a shutter 122A can be positioned in system 100 and out of the optical path 112 of the eye such that light is able to be transmitted to and from the patient's eye along the optical axis 112. After adaptive optic 110 has been adjusted so that all of the light rays from source beam 104 hit substantially a same point on the retina, shutter 122A can be moved into the optical path 112 of the patient's eye so that light can not enter or exit the patient's eye and a second shutter 122B can then be moved out of the path of a perfect eye assembly 124 so that light reflected off of beam splitter 116 from the adjusted adaptive optic 110 can be directed into the perfect eye assembly 124.

In the illustrated embodiment, perfect eye assembly 124 comprises lens 125 and a retina 126, such as a diffuse back scattering surface. It should be appreciated however, that other types of perfect eye assemblies may be used. The light directed from the adjusted adaptive optic 110 may enter the perfect eye and reflect off retina 126 and into a optical path of imaging assembly 118. Since perfect eye assembly 124 does not introduce any aberrations into the light rays that are transmitted from adaptive optic 110, the light rays reflecting off of perfect eye assembly 124 and onto the measuring system 118 will not hit in a substantially same point. The deflection of the rays off of a single point will be caused by the adjusted shape of adaptive optic 110. The deflected light rays that reflect off retina 126 may be imaged by measuring system 118. The deflection of the light rays may provide information as to the wavefront errors imparted by adjusted shape of the adaptive optic 110. Similar to above, the wavefront errors imparted by adaptive optic 110 will be opposite of the errors of the patient's eye. From the shape of the adaptive optic 110, the wavefront errors of the eye may be determined, as described above.

Figure 6:
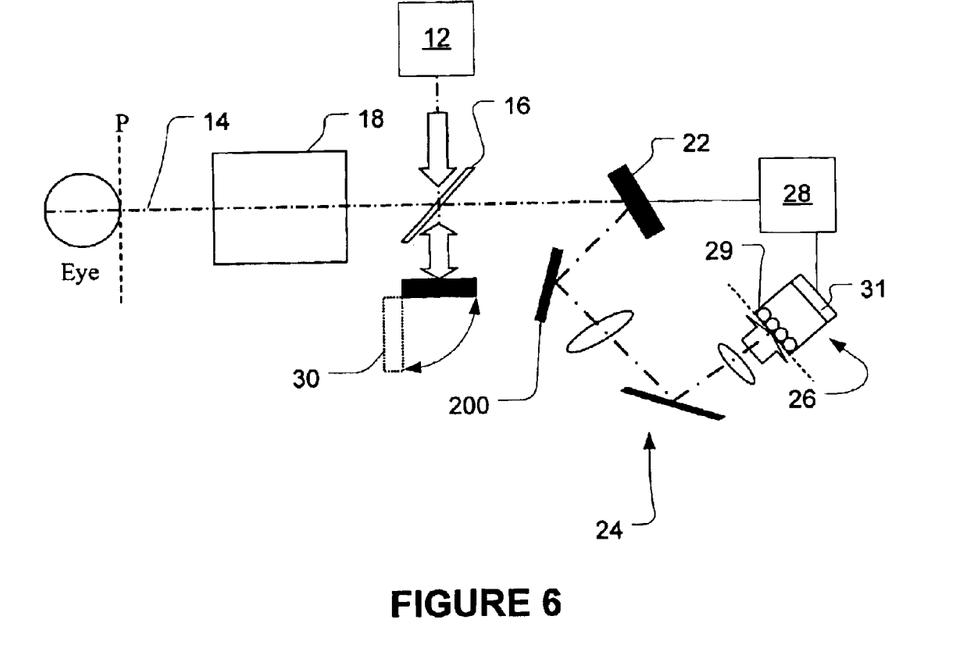
FIG. 6 illustrates an alternative embodiment of a wavefront measurement system that comprises a tipped adaptive optic.

Furthermore, while the above description has been described in the context of measuring wavefront errors of a human eye, the above concepts may be useful in measuring wavefront errors in other target optical systems. Although the foregoing invention has been described in detail for purposes of clarity of understanding, it will be obvious that certain modifications may be practiced within the scope of the appended claims. For example as shown in FIG. 6, in some embodiments of the present invention, it may be possible to tip adaptive optic 22 such that a beam splitter 20 is not used. The "tipping" of mirror 22 separates the light into in and out paths and may use a 100% mirror 200 to direct the light to the aberration sensors 26.

What is claimed is:

1. A method for measuring an optical aberration of an eye, the method comprising:
    transmitting light from the eye along an optical path to an aberration sensor, wherein an adaptive optic is disposed along the optical path between the eye and the aberration sensor;
    adjusting the adaptive optic in response to a signal generated by the aberration sensor so as to provide a desired sensed aberration; and
    determining the shape of the adjusted adaptive optic with the aberration sensor by transmitting an adaptive optic measurement beam onto the adjusted adaptive optic and along the optical path to the aberration sensor.

2. The method of claim 1, wherein the measurement beam comprises a collimated beam of light.

3. The method of claim 2, further comprising introducing the measurement beam to a beamsplitter disposed along the optical path between the eye and the adaptive optic.

4. The method of claim 3, wherein the measurement beam is introduced by directing the measurement beam toward a first side of the beamsplitter so that the beamsplitter directs the measurement beam toward the adaptive optic, and further comprising directing an illumination beam toward a second side of the beamsplitter so that the beamsplitter directs the illumination beam toward the eye.

5. The method of claim 4 comprising stopping transmission of illumination beam before transmitting the measurement beam along the optical path.

6. The method of claim 5 wherein stopping transmission comprises moving a shutter element into the optical path between the eye and the adaptive optic.

7. The method of claim 1 wherein determining the shape of the adjusted adaptive optic comprises measuring wavefront aberrations in the measurement beam that are imparted by the adaptive optic.

8. The method of claim 7 further comprising using the measured wavefront aberrations that are imparted by the adaptive optic to calculate a wavefront error of the eye, wherein the measured wavefront aberrations that are imparted by the adaptive optic is opposite of the wavefront aberrations of the eye.

9. The method of claim 1 wherein the aberration sensor is a Hartmann-Shack wavefront sensor.

10. The method of claim 1 wherein the adaptive optic is a deformable optical element, wherein adjusting aberrations of the adaptive optic comprises deforming the deformable optical element.

11. The method of claim 1 wherein transmitting the measurement beam comprises reflecting the measurement beam off of a mirror and onto the adaptive optic.

12. The method of claim 1 wherein the measurement beam and the light that is transmitted from the eye are generated by a single light source.

13. The method of claim 1 wherein the measurement beam and the light that is transmitted from the eye are generated by different light sources.

14. The method of claim 1 wherein the transmitted light and the measurement beam comprise substantially the same wavelength.

15. The method of claim 1 wherein the light transmitted from the eye forms a pupil conjugate plane on the adaptive optic and the aberration sensor.

16. The method of claim 1 wherein adjusting the adaptive optic to provide the desired sensed aberration comprises eliminating the aberrations from light that is transmitted from the adaptive optic to the aberration sensor.

17. A method for measuring an optical aberration of a target optical system, the method comprising:

transmitting light from the target optical system along an optical path to an aberration sensor, an adaptive optic being disposed along the optical path between the target optical system and the sensor;

adjusting the adaptive optic in response to a signal generated by the sensor so as to provide a desired sensed aberration; and determining the shape of the adjusted adaptive optic by transmitting an adaptive optic configuration measurement beam onto the adjusted adaptive optic and along the optical path to the aberration sensor.

18. The method of claim 17 wherein the measurement beam comprises a collimated beam of light.

19. The method of claim 17 further comprising introducing the measurement beam to a beamsplitter disposed along the optical path between the target optical system and the adaptive optic.

20. The method of claim 19, wherein the measurement beam is introduced by directing the measurement beam toward a first side of the beamsplitter so that the beamsplitter directs the measurement beam toward the adaptive optic, and further comprising directing an illumination beam toward a second side of the beamsplitter so that the beamsplitter directs the illumination beam toward the target optical system.

21. The method of claim 20 comprising stopping transmission of the illumination beam before transmitting the adaptive optic configuration measurement beam along the optical path.

22. The method of claim 21 wherein stopping transmission comprises moving a shutter element into the optical path between the target optical system and the adaptive optic.

23. The method of claim 17 wherein determining the shape of the adjusted adaptive optic comprises measuring wavefront aberrations in the measurement beam that are imparted by the adaptive optic.

24. The method of claim 23 further comprising using the measured wavefront aberrations that are imparted by the adaptive optic to calculate a wavefront error of the target optical system, wherein the measured wavefront aberrations that are imparted by the adaptive optic is opposite of the wavefront aberrations of the target optical system.

25. The method of claim 17 wherein the aberration sensor is a Hartmann-Shack wavefront sensor.

26. The method of claim 17 wherein the adaptive optic is a deformable mirror, wherein adjusting aberrations of the adaptive optic comprises deforming the deformable optical element.

27. The method of claim 17 wherein transmitting the measurement beam comprises reflecting the measurement beam off of a mirror and onto the adaptive optic.

28. The method of claim 17 wherein the measurement beam and the light that is transmitted from the target optical system are generated by a single light source.

29. The method of claim 17 wherein the measurement beam and the light that is transmitted from the target optical system are generated by different light sources.

30. The method of claim 17 wherein the transmitted light and the measurement beam comprise the same wavelength.

31. The method of claim 17 wherein the light transmitted from the target optical system forms a target optical system conjugate plane on the adaptive optic and the aberration sensor.

32. The method of claim 17 wherein adjusting the adaptive optic to provide the desired sensed aberration comprises eliminating the aberrations from light that is transmitted from the adaptive optic to the aberration sensor.

33. A system for measuring optical aberrations of an eye, the system comprising:

an aberration sensor positioned along an optical path that is oriented for receiving light transmitted from the eye;

an adaptive optic disposed along the optical path between the eye and the aberration sensor;

a feedback controller that adjusts the adaptive optic in response to a feedback signal generated by the aberration sensor so as to provide a desired sensed aberration; and an adaptive optic measurement beam source positioned to deliver a measurement beam on the optical path to the adjusted adaptive optic and the aberration sensor, wherein the feedback controller receives a configuration signal from the aberration sensor that is generated in response to aberrations imparted into the measurement beam by the adjusted adaptive optic, wherein the feedback controller determines optical aberrations of the eye by determining the configuration of the adjusted adaptive optic based on the aberrations in the measurement beam that are sensed by the aberration sensor.

34. The system of claim 33 wherein the feedback controller determines high order aberrations of the eye based on the configuration of the adjusted adaptive optic.

35. The system of claim 34 wherein the configuration beam comprises a collimated beam of light.

36. The system of claim 33 further comprising at least one beam splitter positioned in the optical path between the eye and the adaptive optic.

37. The system of claim 36 wherein the at least one beam splitter comprises a first beam splitter and a second beam splitter.

38. The system of claim 33 comprising a movable mirror that reflects a collimated beam of light onto the active mirror.

39. The system of claim 33 wherein the adaptive optic is an active or deformable mirror.

40. The system of claim 33 wherein the aberration sensor is a Hartmann-Shack sensor assembly.

41. The system of claim 33 wherein the configuration beam source is further configured to deliver an eye measurement source beam.

42. The system of claim 33 further comprising a eye measurement source for transmitting the eye measurement source beam.

43. The system of claim 33 further comprising compensation optics positioned within the optical path.

44. The system of claim 33 wherein the desired sensed aberration is a configuration beam comprising no aberrations.

45. A method for measuring optical aberrations of an eye, the method comprising:

reflecting an illumination light off of a retina of the eye, wherein the reflected light contains optical aberrations of optical tissues of the eye;

directing the reflected light toward an adaptive optic;

directing the reflected light from the adaptive optic onto an aberration sensor;

adjusting the adaptive optic until the optical errors in the reflected light directed onto the aberration sensor is substantially nulled;

directing an adaptive optic measurement beam onto the adjusted adaptive optic, wherein the adaptive optic measurement beam is directed off the adjusted adaptive optic and onto the aberration sensor;

measuring the optical aberrations imparted into the adaptive optic measurement beam by the adjusted adaptive optic; and measuring the optical aberrations of the eye by taking a negative of the optical aberrations imparted into the adaptive optic measurement beam by the adjusted adapted optic.

46. The method of claim 45 wherein the adaptive measurement beam comprises collimated light that has no optical aberrations.

47. The method of claim 45 wherein adjusting the adaptive optic comprises deforming a shape of the adaptive optic.

48. The method of claim 45 wherein the aberration sensor comprises a Hartmann-Shack assembly.

* * * * *